US009084562B2

(12) United States Patent
Kakuma

(10) Patent No.: US 9,084,562 B2
(45) Date of Patent: Jul. 21, 2015

(54) CONTROL DEVICE, CONTROL METHOD AND CONTROL PROGRAM FOR OPTICAL COHERENCE TOMOGRAPHIC IMAGE-GENERATING APPARATUSES

(75) Inventor: Hideo Kakuma, Chiba (JP)

(73) Assignee: The Yoshida Dental Mfg. Co., Ltd., Tokyo (JP)

( * ) Notice: Subject to any disclaimer, the term of this patent is extended or adjusted under 35 U.S.C. 154(b) by 131 days.

(21) Appl. No.: 14/008,692

(22) PCT Filed: Jan. 16, 2012

(86) PCT No.: PCT/JP2012/050744
§ 371 (c)(1),
(2), (4) Date: Sep. 30, 2013

(87) PCT Pub. No.: WO2012/132499
PCT Pub. Date: Apr. 10, 2012

(65) Prior Publication Data
US 2014/0192323 A1      Jul. 10, 2014

(30) Foreign Application Priority Data
Mar. 31, 2011    (JP) .................................. 2011-076956

(51) Int. Cl.
*A61B 3/14* (2006.01)
*A61B 3/10* (2006.01)
(52) U.S. Cl.
CPC ....................................... *A61B 3/102* (2013.01)
(58) Field of Classification Search
CPC ........ A61B 3/102; A61B 5/0066; A61B 3/14; A61B 3/13; A61B 2019/524; A61B 8/13; A61B 8/4455; A61B 8/483; A61B 19/5234

USPC .................................. 351/206, 246; 356/479
See application file for complete search history.

(56) References Cited

U.S. PATENT DOCUMENTS

| 6,774,364 B2 | 8/2004 | Takagi |
| 7,794,083 B2 | 9/2010 | Tsukada et al. |

(Continued)

FOREIGN PATENT DOCUMENTS

| JP | 2003303567 A | 10/2003 |
| JP | 2004138947 A | 5/2004 |

(Continued)

OTHER PUBLICATIONS

Supplementary European Search Report from EP 12 76 4366 mailing date of Oct. 10, 2014 (3 pages).

(Continued)

*Primary Examiner* — Hung Dang
(74) *Attorney, Agent, or Firm* — Capitol City TechLaw, PLLC

(57) ABSTRACT

To measure internal information on the subject, the OCT (optical coherence tomographic) control device is equipped with: a first imaging control means for initiating imaging when it is determined that input of a measurement instruction to scan the laser light at a prescribed pitch in the imaging target area of a sample using the galvano mirror has been received, and completing imaging in an imaging time that matches the prescribed pitch; and with a second imaging control means for initiating imaging when it is determined that input of a preview instruction to scan at a coarser pitch than the prescribed pitch has been received, and for completing imaging when it is determined that input of a measurement instruction as an instruction to cancel the preview instruction has been received.

11 Claims, 10 Drawing Sheets

(56) References Cited

U.S. PATENT DOCUMENTS

| | | | |
|---|---|---|---|
| 7,869,663 B2 | 1/2011 | Buckland et al. | |
| 7,980,696 B1 * | 7/2011 | Taki et al. | 351/206 |
| 8,442,356 B2 | 5/2013 | Buckland et al. | |
| 2007/0046809 A1 | 3/2007 | Nakamura | |
| 2007/0216909 A1 * | 9/2007 | Everett et al. | 356/479 |
| 2011/0234785 A1 | 9/2011 | Wanda et al. | |
| 2012/0092617 A1 | 4/2012 | Muto et al. | |

FOREIGN PATENT DOCUMENTS

| | | |
|---|---|---|
| JP | 2005352030 A | 12/2005 |
| JP | 3118718 U | 1/2006 |
| JP | 2006343595 A | 12/2006 |
| JP | 2007067574 A | 3/2007 |
| JP | 2008154704 A | 7/2008 |
| JP | 2008175698 A | 7/2008 |
| JP | 2010142428 A | 7/2010 |
| WO | 2007/016397 A2 | 2/2007 |
| WO | 2010/150496 A1 | 12/2010 |

OTHER PUBLICATIONS

International Search Report from PCT/JP2012/050744 mailing date of Feb. 21, 2012 (4 pages).

* cited by examiner

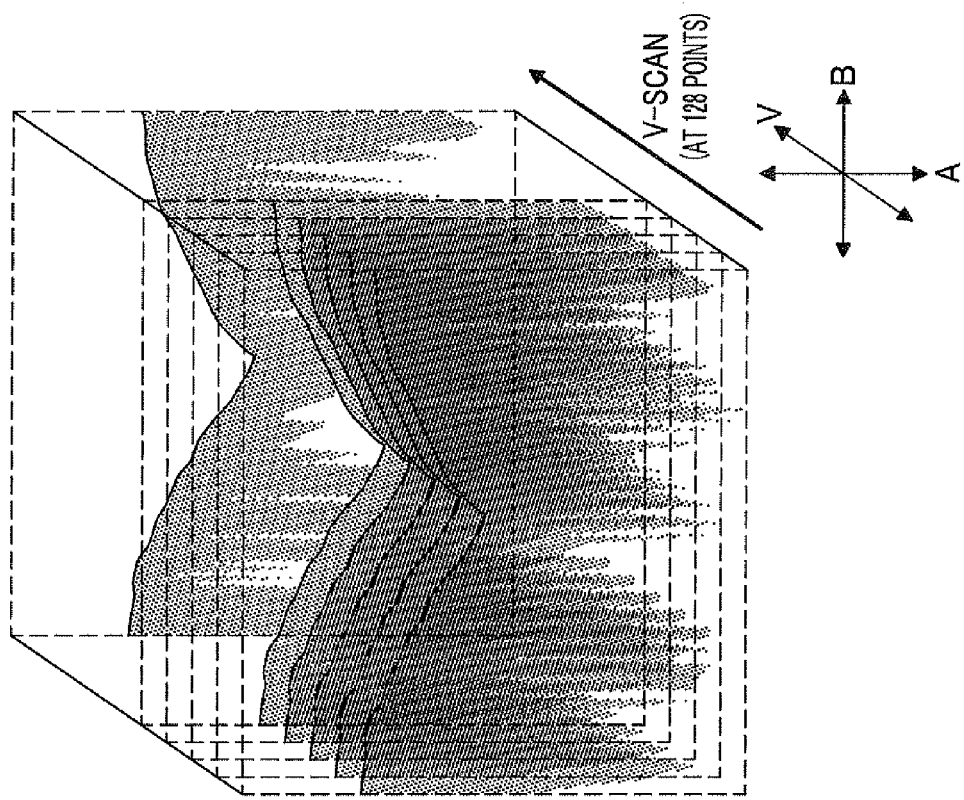
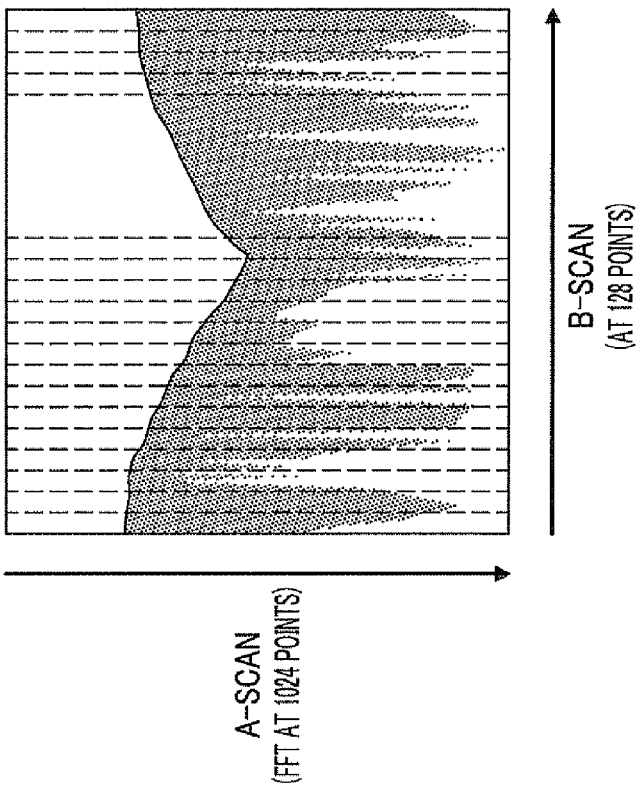

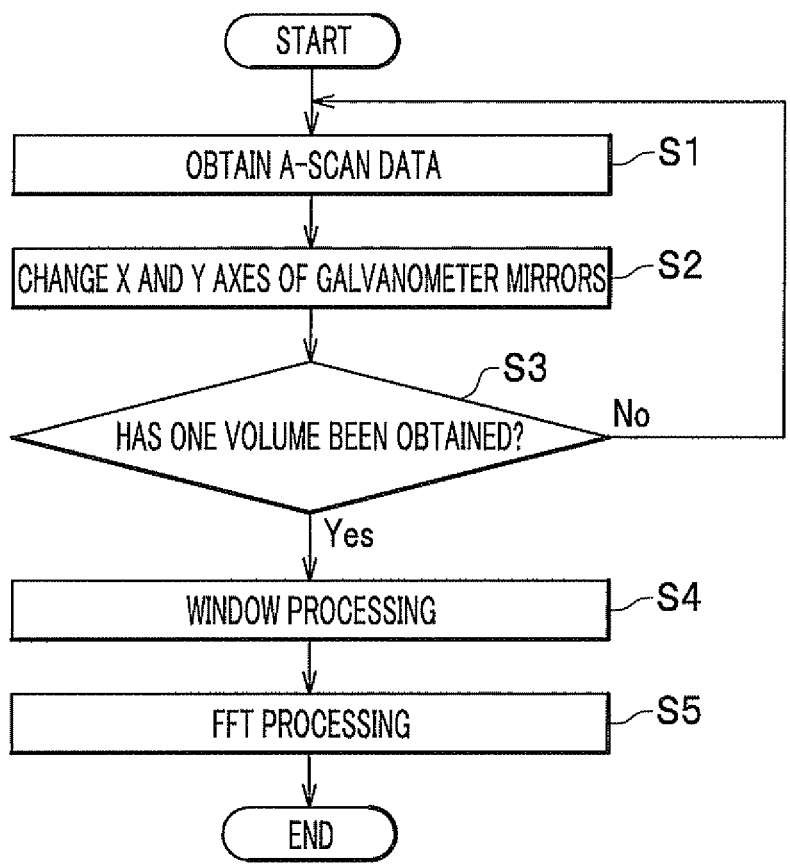

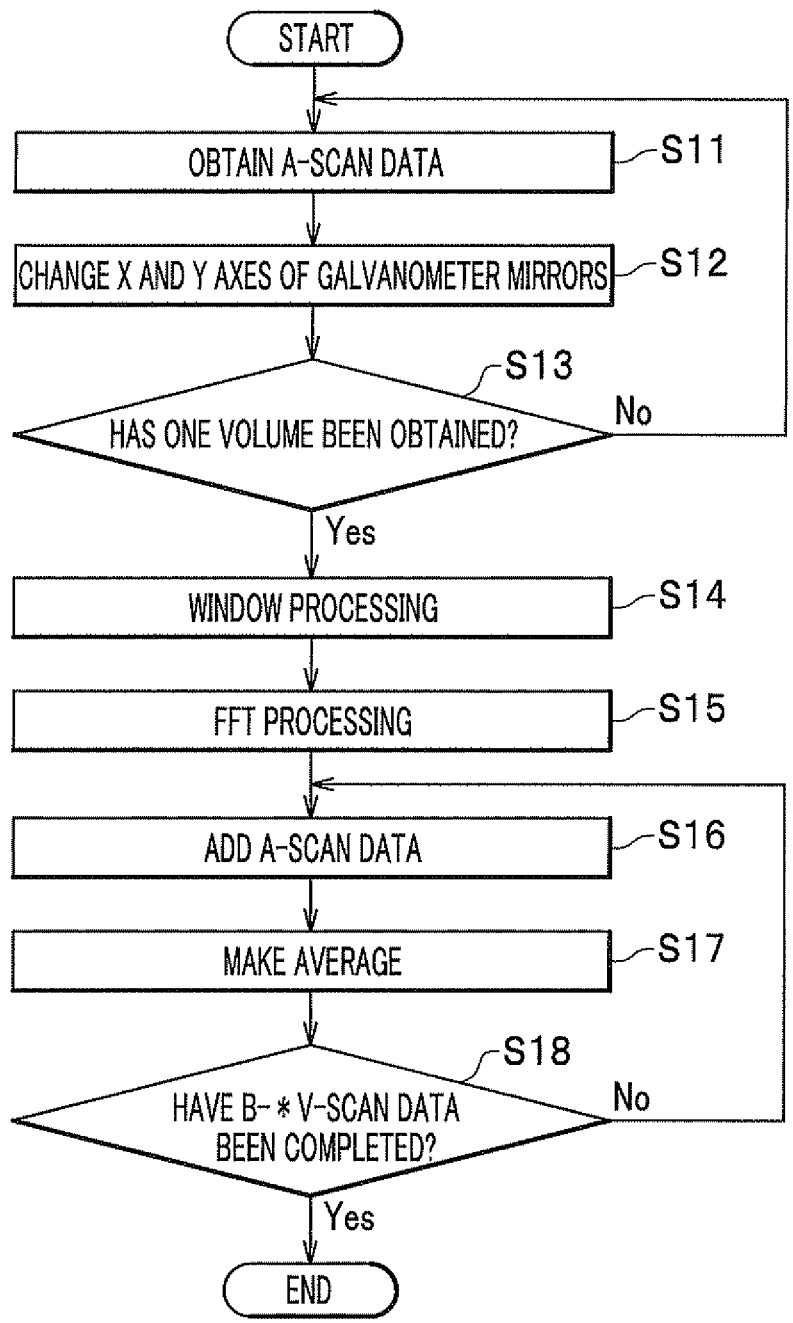

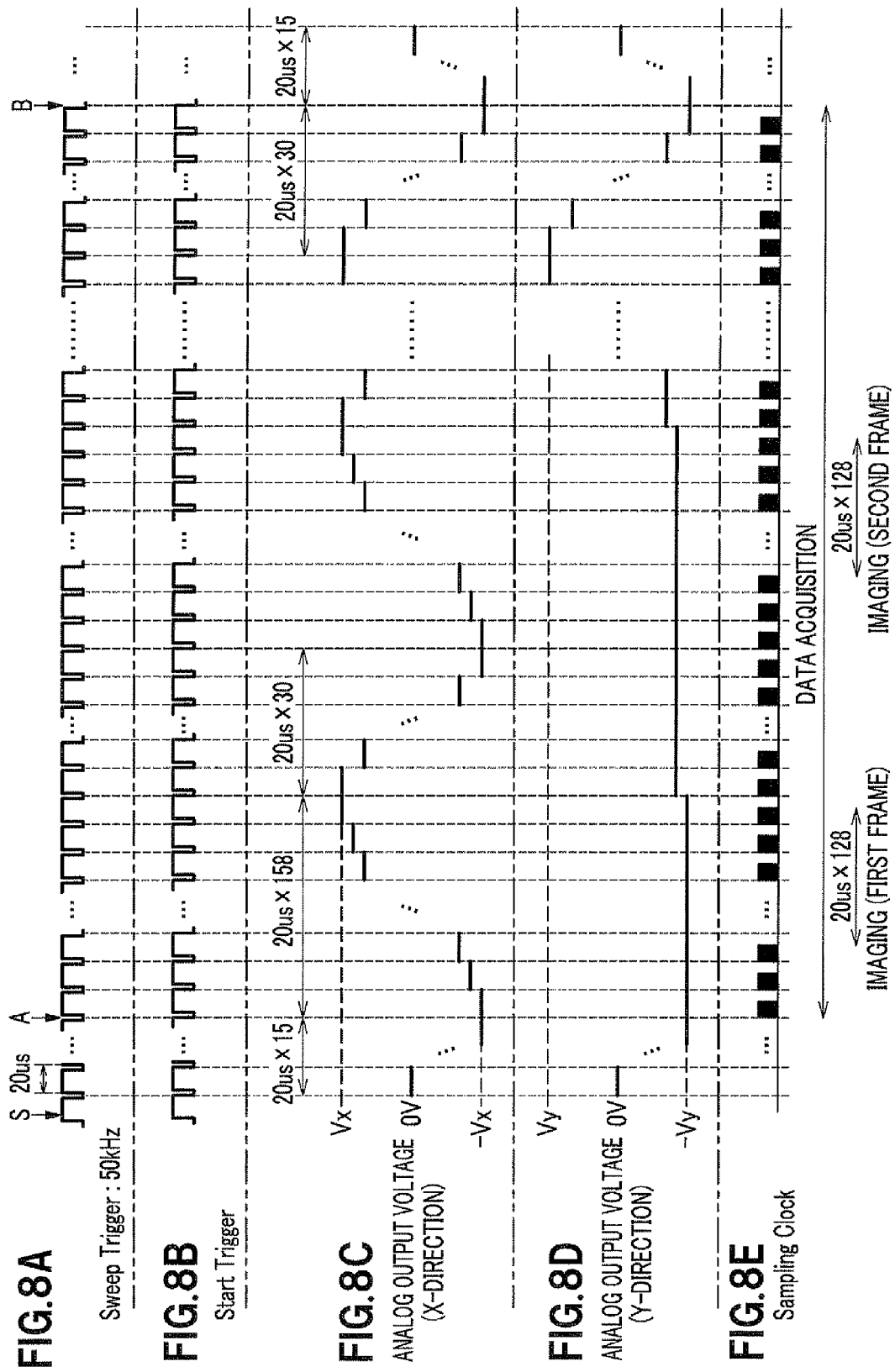

CONTROL DEVICE, CONTROL METHOD AND CONTROL PROGRAM FOR OPTICAL COHERENCE TOMOGRAPHIC IMAGE-GENERATING APPARATUSES

TECHNICAL FIELD

The present invention relates to optical coherence tomography apparatuses, and particularly to a controller, a control method, and a control program for an optical coherence tomography apparatus.

BACKGROUND ART

Conventionally, optical coherence tomography apparatuses (hereinafter, referred to as OCT apparatuses) have been applied to ophthalmic practice such as tomographic imaging of a cornea and/or a retina of an eye in the biomedical fields. The OCT allows for non-invasive and non-contact diagnosis by irradiating a living tissue with light. Examples of a known diagnostic system other than the OCT include: CT (Computed Tomography) with resolution of 200 micrometers or less; MRI (Magnetic Resonance Imaging) with resolution of 800 micrometers or less; and PET (Positron Emission Tomography) with resolution of 1000 micrometers or less. Compared with these systems, the OCT can achieve by far superior resolution from several to several dozens micrometers, and can display a high-resolution precise image. It has been known that the OCT systems can be classified roughly into TD (Time Domain)-OCT and FD (Frequency Domain)-OCT. The latter FD-OCT can be further classified into SD (Spectrum Domain)-OCT and SS (Swept Source)-OCT.

For example, in the SS-OCT, a laser source is used to continuously sweep wavelengths (wave numbers); and spectral information as obtained using a detector is subject to FFT (Fast Fourier Transform) processing to specify an optical path length. The SS-OCT has a higher resolution than X-ray equipment and CT devices, which are widely used in dental practice, and is characterized in that a real-time measurement can be performed without being exposed to radiation.

Meanwhile, the above-described TD-OCT has been tested for dental practice. The SS-OCT, however, can acquire data faster with higher sensitivity than the TD-OCT. Thus, the SS-OCT has a motion artifact (a ghost due to body movement)-resistant feature.

In order to obtain a tomogram, the OCT apparatus requires two-dimensional mechanical scanning in a widthwise direction (a left-right direction with respect to an object) and in a lengthwise direction (a front-rear direction with respect to the object), which are perpendicular to a laser beam direction (a vertical or depthwise direction with regard to the object) facing the object. Unfortunately, the imaging and diagnosis conventionally take a long time.

A technology (see JP2010-142428A) regarding an ophthalmic OCT apparatus has been known that prior to acquisition of a detailed image used for diagnosis, an overview of an object is obtained.

An imaging apparatus disclosed in JP2010-142428A includes: a tomographic image acquisition section whose function is implemented by an OCT apparatus; and a front image acquisition section whose function is implemented by a fundus camera or an SLO (Scanning Laser Ophthalmoscope) to acquire a front image. The front image acquisition section is to obtain an overview of an object.

In addition, in the dental fields, a handpiece for a dental optical diagnostic apparatus includes OCT means. Then, means for positioning an optical diagnosis site in a tooth is implemented by a camera imaging system, which includes an imaging camera for acquiring a surface image (see Japanese Utility Model Registration Application No. 3118718). Accordingly, the camera image can be used for prior positioning.

PRIOR ART REFERENCE

Patent Literatures

Patent Literature 1: JP 2010-142428 A
Patent Literature 2: JP 3118718 U

SUMMARY OF THE INVENTION

Problems To Be Solved By the Invention

However, a conventional apparatus beforehand obtains a surface image while a tomogram should be obtained as an image taken for determination of a detailed image used for diagnosis (detailed imaging). Unfortunately, it takes a long time to acquire a desired tomogram used for diagnosis.

Here, the present invention has resolved the above problems. It is an object of the present invention to provide a controller, a control method, and a control program for an optical coherence tomography apparatus allowing for fast acquisition of a desired tomogram of an object.

Means for Solving the Problems

In order to solve the above problems, the present invention relates to a controller for an optical coherence tomography apparatus, including: an imaging control means for imaging with a predetermined imaging mode based on an external input; and image-processing means for performing image processing of an detection signal as obtained at the imaging, the imaging control means including: a first imaging control means for starting imaging when it is determined to receive an input of a measurement command to scan an imaging range of an object with laser beam at a predetermined pitch by using a scanning mechanism so as to determine internal information of the object and for stopping the imaging after an imaging time according to the predetermined pitch; and a second imaging control means for starting imaging when it is determined to receive an input of a preview command to scan the imaging range with the laser beam at a larger pitch than the predetermined pitch by using the scanning mechanism and for stopping the imaging when it is determined to receive an input of a command to cancel the preview command, wherein the optical coherence tomography apparatus includes: an optical unit including: a light source for periodically emitting the laser beam on the object; and a detector for detecting the internal information of the object; a probe including the scanning mechanism which can perform two-dimensional scanning with the laser beam, the probe guiding the laser beam emitted through the optical unit to the object and guiding light reflected by the object to the optical unit; and a control unit including: the controller for controlling generation of an optical coherence tomogram of the object from data converted from the detection signal of the detector while performing imaging by controlling the scanning mechanism in synchrony with the laser beam; and a display for displaying the optical coherence tomogram.

According to such a configuration, the controller for the optical coherence tomography apparatus uses the first imaging control means to start imaging the object when receiving the measurement command. Next, the controller uses the image-processing means to perform image processing of the detection signal as obtained using the scanning mechanism by scanning the object with laser beam at a predetermined pitch. Then, the display displays an optical coherence tomogram of the object at a predetermined resolution. At this time, the imaging is terminated after an imaging time according to a scanning pitch of the scanning mechanism. Consequently, after completion of the imaging, the display displays a still image of the optical coherence tomogram. Here, when a rectangular imaging range is segmented into 300 points in length and width and the measurement is performed for imaging, for example, the scanning mechanism repeats a small movement and stop 300 times per side. When the measurement for imaging is performed at these 300 points, it takes a shorter period to complete imaging than that at 400 points. In addition, the controller for the optical coherence tomography apparatus uses the second imaging control means to start imaging the object when receiving the preview command. Next, the controller uses the image-processing means to perform image processing of the detection signal as obtained using the scanning mechanism by scanning the object with the laser beam at a larger pitch than the predetermined pitch. Then, the display displays an optical coherence tomogram of the object at a lower resolution than the predetermined resolution. When the optical coherence tomogram is displayed by the preview command, the detection signal is used that has been obtained by scanning the object at a larger pitch than that used in the optical coherence tomogram displayed by the measurement command. Accordingly, the optical coherence tomogram can be displayed faster. For example, a rectangular imaging range is segmented into 128 points in length and width and the preview imaging is performed. At that time, it takes a shorter period to complete imaging than that at 300 points or 400 points. In addition, with regard to the optical coherence tomogram at a low resolution, the imaging and image processing continue until a command to cancel the preview command is input. Accordingly, the optical coherence tomogram obtained can be displayed as a real-time moving image. Note that no resolution variation is observed in a direction along an optical axis toward the object.

In addition, the controller for an optical coherence tomography apparatus according to an embodiment of the present invention preferably includes a foot controller connected to the imaging control means in wired or wireless communication in a configuration having received an input of the preview command and an imaging command, the foot controller including a first switch and a second switch, wherein when a user uses his/her foot to operate either the first switch or the second switch, the imaging control means is informed of a first or second switch signal corresponding to the first or second switch; when the second imaging control means receives an input of the first switch signal from the foot controller, it is determined to receive an input of the preview command; when the second imaging control means receives an input of the second switch signal from the foot controller, it is determined to receive an input of a command to cancel the preview command; and when the first imaging control means receives an input of the second switch signal from the foot controller, it is determined to receive an input of the measurement command.

In such a configuration, the controller for the optical coherence tomography apparatus uses the second imaging control means to determine that an input of the preview command is received when a user uses his/her foot to operate the first switch of the foot controller. In addition, the controller uses the first imaging control means to determine that an input of the measurement command is received while canceling the preview command when the user uses his/her foot to operate the second switch of the foot controller. This configuration allows the user to press the foot controller by his/her foot when the user makes a diagnostic probe section contact a patient during imaging even if his/her both hands are occupied. This makes it possible to input the preview command and/or the measurement command even in the above situation. This improves operability.

Further, the controller for an optical coherence tomography apparatus according to an embodiment of the present invention preferably includes scanning-area-selection-controlling means for controlling selection of a range scanned by the scanning mechanism according to an area of interest, wherein the area is selected by the user from a plurality of predetermined different areas as imaging ranges for the object; and the area is input to the imaging control means.

In such a configuration, the controller for the optical coherence tomography apparatus can use the scanning-area-selection-controlling means to control and select the range scanned by the scanning mechanism according to the area selected by the user from the plurality of the different areas. This improves operability. In such a configuration, the controller for the optical coherence tomography apparatus may have the fixed number at which the small movement and stop of the scanning mechanism is repeated so as to take a series of images of the object. At that time, changing the area of the imaging range enables the scanning pitch of the scanning mechanism to be changed. This can increase resolution of the image obtained. For example, a small rectangular imaging range may be segmented into 400 points in length and width. That case should have a higher resolution than the case where a large rectangular imaging range is segmented into 400 points in length and width. Accordingly, an image is taken with the widest range. Next, an area of interest on the object is targeted. Then, the image is narrowed to the smallest range. This procedure makes it possible to display the targeted area of interest at a higher resolution.

Furthermore, in the controller for an optical coherence tomography apparatus according to an embodiment of the present invention, the image-processing means preferably uses data obtained by taking an image of the object to generate: an optical coherence tomogram with respect to a tomographic plane in a direction along an optical axis toward the object; a two-dimensional image with respect to a scanning plane perpendicular to the optical axis toward the object; and a three-dimensional image of the object, wherein the image-processing means controls and displays each generated image on one page of the display as image information regarding the object.

Such a configuration makes it possible for the controller for the optical coherence tomography apparatus to display the optical coherence tomogram, the two-dimensional image with regard to the scanning plane of the object, and the three-dimensional image of the object on one page of the display. Accordingly, the user can intuitively recognize which part of the object and which tomographic plane the displayed optical coherence tomogram represents.

In addition, in the controller for an optical coherence tomography apparatus according to an embodiment of the present invention, the image-processing means preferably generates, as the two-dimensional image with regard to the scanning plane perpendicular to the optical axis toward the object, an en-face image which combines information on the surface of the object irradiated with the laser beam and information on the object in a direction along the optical axis.

Such a configuration allows the controller for the optical coherence tomography apparatus to construct the two-dimensional image with respect to the scanning plane of the object, which two-dimensional image is displayed together with the optical coherence tomogram and the three-dimensional image of the object, from data obtained using image-processing of the signal detected by the OCT. Consequently, not only information on the outer surface of the object but also internal information is superimposed to construct the two-dimensional image. Thus, this two-dimensional image can be used for measurement and/or diagnosis. Also, such a configuration circumvents a need to install a camera member, etc., specialized for obtaining a two-dimensional image with regard to a scanning plane of the object. Because of this, for example, a camera does not have to be installed in a probe, so that the probe can be made smaller.

Moreover, the present invention relates to a method for controlling an optical coherence tomography apparatus, including the steps of: stating imaging when it is determined to receive an input of a measurement command to scan an imaging range of an object with laser beam at a predetermined pitch by using a scanning mechanism so as to determine internal information of the object and stopping the imaging after an imaging time according to the predetermined pitch, as one of predetermined imaging modes based on an external input for a controller; starting imaging when it is determined to receive an input of a preview command to scan the imaging range with the laser beam at a larger pitch than the predetermined pitch by using the scanning mechanism and stopping the imaging when it is determined to receive an input of a command to cancel the preview command, as another of the predetermined imaging modes based on an external input for the controller; and image-processing a detection signal as obtained by the imaging of either imaging mode, wherein the optical coherence tomography apparatus includes: an optical unit including: a light source for periodically emitting the laser beam on the object; and a detector for detecting the internal information of the object; a probe including the scanning mechanism which can perform two-dimensional scanning with the laser beam, the probe guiding the laser beam emitted through the optical unit to the object and guiding light reflected by the object to the optical unit; and a control unit including: the controller for controlling generation of an optical coherence tomogram of the object from data converted from the detection signal of the detector while performing imaging by controlling the scanning mechanism in synchrony with the laser beam; and a display for displaying the optical coherence tomogram.

According to such a procedure, first, the method for controlling an optical coherence tomography apparatus can use a preview command to display an optical coherence tomogram at a low resolution, that is, an image at a desired tomographic plane, by using the detection signal as obtained by scanning the object with laser beam at a larger pitch. Next, the preview command can be canceled. Then, the method can use a measurement command to display an optical coherence tomogram at a high resolution, that is, an image at the desired tomographic plane, by using a detection signal as obtained by scanning the object with the laser beam with a smaller pitch. Note that the measurement command may include a command to cancel the preview command. Also, such a procedure, for example, makes it possible to beforehand obtain, at a lower resolution, an optical coherence tomogram similar to an optical coherence tomogram used for measurement and/or diagnosis by using the preview command. Besides, the preview command can be used to make it easy to repeatedly display different optical coherence tomograms at a low resolution. Accordingly, the user can quickly find out a desired tomographic plane as a tomogram of the object. This information can be used to allow for fast acquisition of a desired tomogram at a high resolution.

Finally, the present invention relates to a program for controlling an optical coherence tomography apparatus, in which each means of the controller for an optical coherence tomography apparatus according to the above is used to make a computer function. Such a configuration enables each function based on this program to be implemented in the computer having this program installed thereon.

Effect of the Invention

The present invention makes it possible for a controller for an optical coherence tomography apparatus to quickly obtain a desired tomogram of an object.

BRIEF DESCRIPTION OF THE DRAWINGS

FIG. 1A illustrates an apparatus with a single-joint arm;

FIG. 1B illustrates an apparatus with a multiple-joint arm;

FIG. 4A describes types of recording area;

FIG. 4B is a schematic diagram illustrating an optical path of laser beam which passes through the inside of a diagnostic probe;

FIGS. 5A-5B illustrate how to generate OCT images by means of an OCT controller according to an embodiment of the present invention;

FIG. 5A is an image showing internal information as obtained along with an A-scan and a B-scan of a sample;

FIG. 5B is images showing internal information as obtained along with an A-scan, a B-scan, and a V-scan;

FIG. 6 is a flowchart illustrating how to perform processing so as to display an OCT image by using an OCT controller according to an embodiment of the present invention;

FIG. 7 is a flowchart illustrating how to perform processing so as to display an en-face image by using an OCT controller according to an embodiment of the present invention;

FIGS. 8A-8E show an example of a timing chart for image-processing by an OCT controller according to an embodiment of the present invention;

FIG. 8A illustrates a sweep trigger for a light source output;

FIG. 8B illustrates a start trigger for a D/A converter circuit output;

FIGS. 8C and 8D illustrate analog output voltages in X and Y directions as output from a galvanometer mirror control circuit;

FIG. 8E illustrates a clock to generate an OCT image;

EMBODIMENTS FOR CARRYING OUT THE INVENTION

Figure 1B:
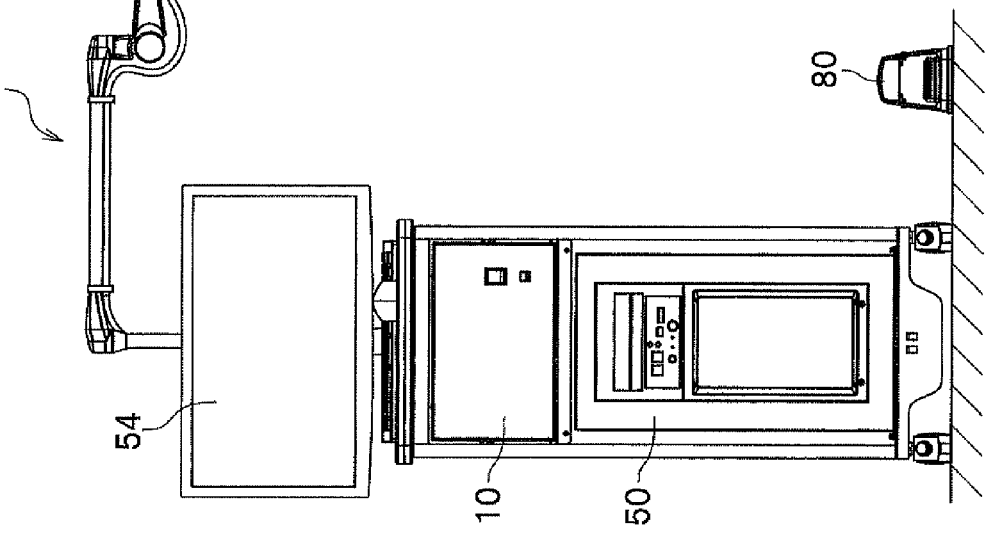
FIGS. 1A-1B are outline views of optical coherence tomography apparatuses according to embodiments of the present invention.

Hereinafter, modes to implement apparatuses of the present invention (hereinafter, referred to as an "embodiment") are described in detail by referring to the drawings. The following details each section as follows: 1. Overview of OCT Apparatus Configuration; 2. How to Configure OCT Controller; 3. How OCT Controller Works; and 4. Screen Display Examples of Display.

1. Overview of OCT Apparatus Configuration

Figure 1A:
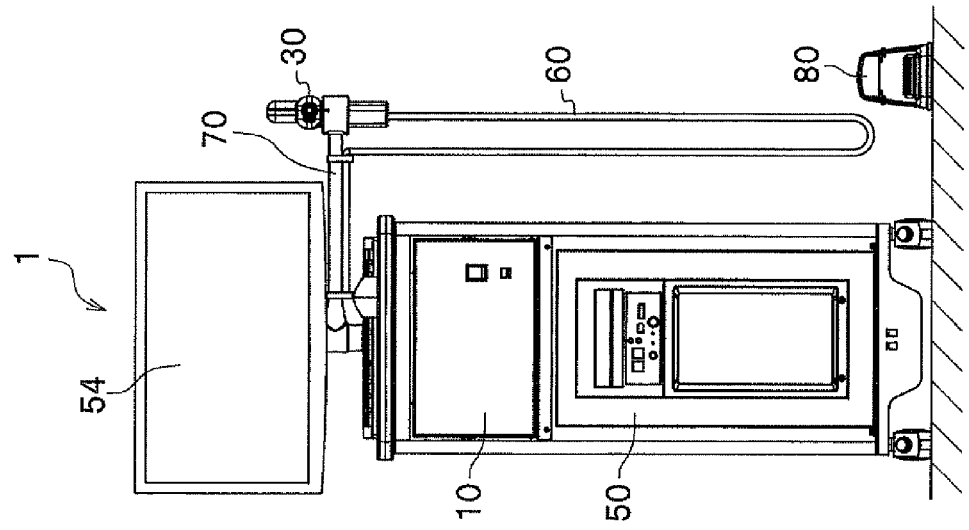
Figure 2:
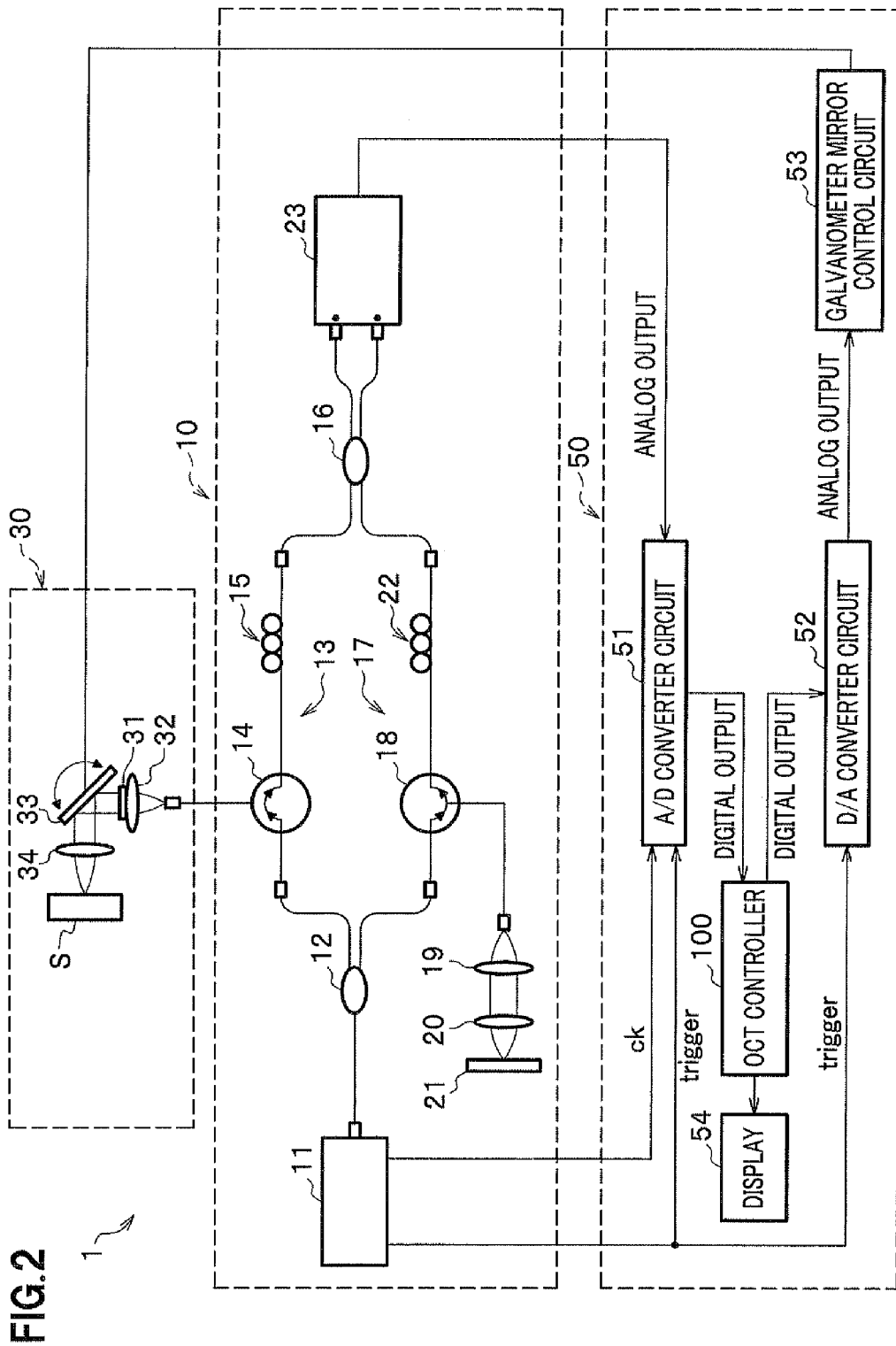
FIG. 2 is a schematic view illustrating how to configure units for an optical coherence tomography apparatus according to an embodiment of the present invention.

With reference to FIGS. 1A, 1B, and 2, the following describes an overview of an OCT (optical coherence tomography) apparatus configuration in which an object imaged by the OCT apparatus is a dental patient's tooth of interest in diagnosis. As illustrated in FIGS. 1A, 1B, and 2, an OCT apparatus 1 primarily includes: an optical unit section (optical unit) 10; a diagnostic probe section (probe) 30; and a control unit section (control unit) 50.

Optical Unit Section

The optical unit section (optical unit) 10 includes a light source, an optical system, and a detector section, to all of which each type of common optical coherence tomography is applicable. FIG. 2 shows that the optical unit section 10 includes: a light source 11 which periodically emits laser beam on a sample (object) S; a detector 23 which detects internal information of the sample S; and optical fibers and various optical components which are disposed partway through an optical path between the light source 11 and the detector 23.

The following describes how the optical unit section 10 looks like in general.

A coupler 12, light-splitting means, is used to split light emitted from the light source 11 into measurement light and reference light. The measurement light enters the diagnostic probe section 30 via a circulator 14 in a sample arm 13. When a shutter 31 of the diagnostic probe section 30 is open, this measurement light passes through a collimator lens 32 and a galvanometer mirror (scanning mechanism) 33 and is focused on a sample S by a condensing lens 34. Next, the measurement light is scattered and reflected on the Sample S. Then, the measurement light passes through the condensing lens 34, the galvanometer mirror 33, and the collimator lens 32. After that, the measurement light returns to the circulator 14 of the sample arm 13. Finally, the returned measurement light is input via a coupler 16 into a detector 23.

Meanwhile, the reference light split by the coupler 12 passes from a circulator 18 of a reference arm 17 through a collimator lens 19, and is focused on a reference mirror 21 by a condensing lens 20. Next, the reference light is reflected on the reference mirror. Then, the reference light passes through the condensing lens 20 and the collimator lens 19. After that, the reference light returns to the circulator 18. Finally, the returned reference light is input via the coupler 16 into the detector 23. That is, the coupler 16 couples the returned measurement light which has been scattered and reflected on the sample S and the reference light which has been reflected by the reference mirror 21. Accordingly, light (interference light) which has been coupled and interfered can be detected by the detector 23 as internal information of the sample S. Meanwhile, in the OCT apparatus 1 including the diagnostic probe section 30, light may be polarized. In order to reduce the polarization, the sample arm 13 and the reference arm 17 have installed therein a polarization controller 15 and a polarization controller 22, respectively.

For example, an SS-OCT-type laser source can be used for the light source 11.

In this case, the light source 11 preferably has performance characteristics such as a center wavelength of 1310 nm, a sweep wavelength width of 100 nm, a sweep rate of 50 kHz, and a coherence length of 14 mm. As used herein, the coherence length corresponds to a distance when the power spectrum is attenuated by 6 dB from the top. Note that the coherence length is preferably from 10 mm to less than 48 mm, which is for high-coherence light. The coherence length, however, is not limited to the above range. When the object is, for example, a molar, it is preferable to obtain data at a deeper position in its depthwise direction (in an optical axis direction). The coherence length of 10 mm or more enables something (e.g., caries) specific to a tooth to be imaged. In addition, it is theoretically possible for an OCT apparatus to carry a light source allowing for a coherence length of 48 mm or more. The foregoing light source is an SS-OCT-type one in which a wave number (wavelength) is swept stepwise. Thus, if all-round performance including a sweep rate and resolution is sought for this light source, it is difficult to manufacture the light source itself. Accordingly, it is practical to set the coherence length to less than 48 mm.

Diagnostic Probe Section

The diagnostic probe section (probe) 30 includes a galvanometer mirror (scanning mechanism) 33 in which laser beam is used to perform two-dimensional scanning. The diagnostic probe section 30 guides the laser beam from the optical unit section 10 to the sample S and also guides light reflected by the sample S to the optical unit section 10.

A cable 60 (see FIGS. 1A and 1B) is used to connect the diagnostic probe section 30 to the optical unit section 10 and a control unit section 50. The cable 60 has optical fibers which are connected to the optical unit section 10 and communication lines which are connected to the control unit section 50.

In one hand, when not used for imaging, the diagnostic probe section 30 is kept on a holder as illustrated in FIG. 1A. The holder is at the tip of the single-joint arm 70 which extends horizontally from a lower side of a display 54. The display is arranged above the OCT apparatus 1. This configuration allows even the long cable 60 to be held without torsion during keeping, thereby reducing a keeping space.

On the other hand, when used for imaging, the diagnostic probe section 30 is held by the user while removing it from the holder of the single-joint arm 70. The user makes the diagnostic probe section 30 contact a patient so as to stabilize image, etc. In order to manipulate an imaging start button even if the user already uses his/her both hands, the user can still use a foot controller 80 (see FIGS. 1A and 1B) which is connected to the control unit section 50 in wired or wireless communication.

An OCT apparatus 1A illustrated in FIG. 1B has the same configuration as in the OCT apparatus 1 illustrated in FIG. 1A except that: the diagnostic probe section 30 can be held on a holder at the tip of a multiple-joint arm 70A which extends horizontally from an upper side of the display 54 disposed above the OCT apparatus 1A. The multiple-joint arm 70A is longer from the base end to the tip and is arranged at a higher position from the floor than the single-joint arm 70. Accordingly, the cable 60 can hang down less. Thus, the cable 60 does not reach the floor. Examples of this advantage include that the cable is sanitary. In addition, this can improve operability and can prevent the user from inadvertently stepping on the dangling cable 60.

Figure 4A:
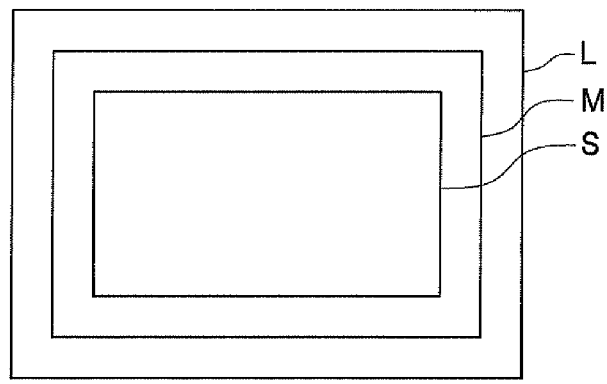
FIGS. 4A-4B illustrate how to take an image by using an optical coherence tomography apparatus according to an embodiment of the present invention.
Figure 4B:
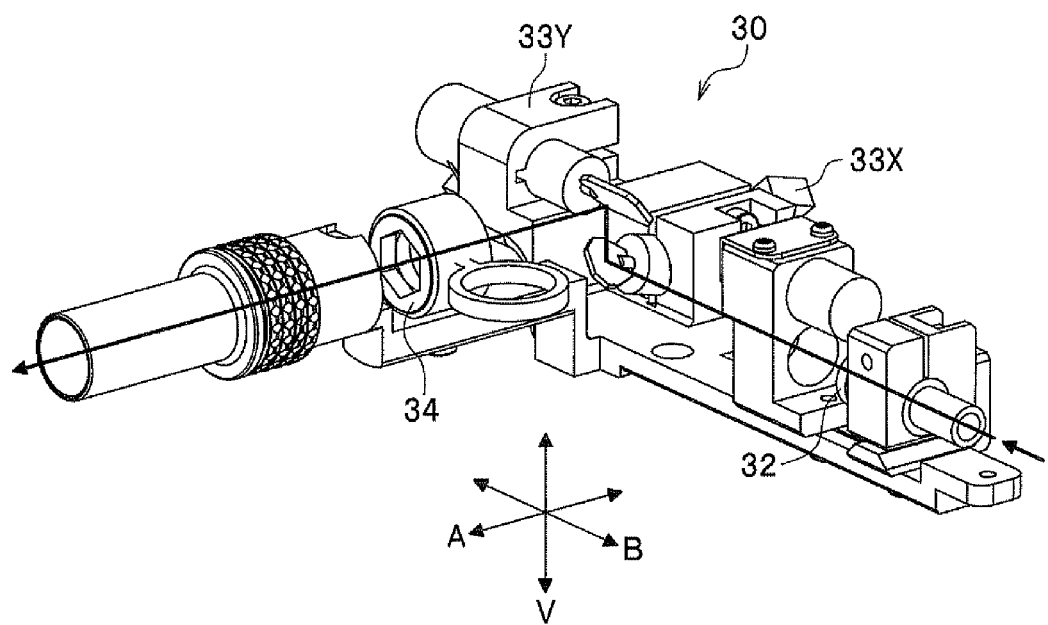

As detailed in FIG. 4B, the galvanometer mirror 33 installed in the diagnostic probe section 30 includes a galvanometer mirror 33X in an X-direction and a galvanometer mirror 33Y in a Y-direction. The sample S (see FIG. 2; the same applies to the following) is irradiated via the galvanometer mirror 33X and the galvanometer mirror 33Y with the laser beam emitted by the light source 11. The detector 23 obtains internal information in a depthwise direction (A direction) which goes inside the sample S from its surface facing the nozzle tip (the left end in FIG. 4B) of the diagnostic probe section 30. As described below, one scanning produces data in an A-direction (hereinafter, referred to as A-scan data) at 1152 points. Subsequently, image processing on frequency analysis (i.e., FFT processing) is carried out. Then, data at 1024 points (hereinafter, referred to as A-scan (FFT at 1024 points)) are each obtained as an FFT processing output on data in an A-direction.

As used herein, the X-direction and the Y-direction correspond to a lateral direction (an X-axis direction; a left-right direction in FIG. 4B) and a longitudinal direction (a Y-axis direction; a top-bottom direction in FIG. 4B) with respect to the surface of the sample S facing the nozzle tip (the left end in FIG. 4B) of the diagnostic probe section 30 (see FIG. 4B).

The galvanometer mirror 33X is disposed at a collimator lens 32 side. With regard to the galvanometer mirror 33X, a motor drives and rotates a mirror plane (A-V plane) by using an A-direction as an axis. At this time, the data obtained are lateral data (in an X-axis direction) with regard to the surface of the sample S and are thus data in a B-direction. If the motion rotation angle of the galvanometer mirror is, for example from −3 degrees to +3 degrees and data at 128 points in a B-direction are required, data at 158 points in a B-direction (hereinafter, referred to as B-scan data) are obtained as described below.

The galvanometer mirror 33Y is disposed at a condensing lens 34 side, and a motor drives and rotates a mirror plane (B-V plane) by using an B-direction as an axis. At this time, the data obtained are longitudinal data (in a Y-axis direction) with regard to the surface of the sample S and are thus data in a V-direction (hereinafter, referred to as V-scan data).

Control Unit Section

As illustrated in FIG. 2, the control unit section (control unit) 50 includes: an A/D converter circuit 51; a D/A converter circuit 52; a galvanometer mirror control circuit 53; a display 54; and an OCT controller 100.

The A/D converter circuit 51 converts analog output signals from the detector 23 into digital signals. In an embodiment according to the present invention, the A/D converter circuit 51 starts collecting signals in synchrony with triggers output from the light source 11 which is a laser output device. Likewise, in synchrony with timings of clock signals ck output from the laser output device, the A/D converter circuit 51 collects and converts analog output signals from the detector 23 into digital signals. The OCT controller 100 receives these digital signals.

The D/A converter circuit 52 converts the digital output signals from the OCT controller 100 to analog signals. In an embodiment according to the present invention, the D/A converter circuit 52 is in synchrony with triggers output from the light source 11, which is the laser output device, and converts the digital signals from the OCT controller 100 into analog signals. The galvanometer mirror control circuit 53 receives these analog signals.

The galvanometer mirror control circuit 53 is a driver which controls the galvanometer mirror 33 of the diagnostic probe section 30. The galvanometer mirror control circuit 53 is based on the analog output signals from the OCT controller 100 and is in synchrony with the output cycle of laser beam emitted by the light source 11. Accordingly, the galvanometer mirror control circuit 53 outputs a motor driving signal to drive or stop a motor for the galvanometer mirror 33X in an X-direction or the galvanometer mirror 33Y in a Y-direction.

The galvanometer mirror control circuit 53 performs at a different timing a process that rotates an axis of the galvanometer mirror 33X and changes an angle of its mirror plane and a process that rotates an axis of the galvanometer mirror 33Y and changes an angle of its mirror plane. These processes using the galvanometer mirror control circuit 53 are simply called galvanometer mirror X- and Y-axis changes. Examples of the timing to perform the galvanometer mirror X- and Y-axis changes are described below.

The display 54 displays an optical coherence tomogram (hereinafter, referred to as an OCT image) that the OCT controller 100 generates. Examples of the display 54 includes a liquid crystal display (LCD), electronic luminescence (EL), a cathode ray tube (CRT), and a plasma display panel (PDP).

The OCT controller 100 is a controller for the OCT apparatus 1. The OCT controller 100 controls the galvanometer mirror 33 in synchrony with the laser beam to perform imaging and controls how to generate an OCT image of the sample S from data into which the detection signals of the detector 23 are converted.

2. How To Configure OCT Controller

Figure 3:
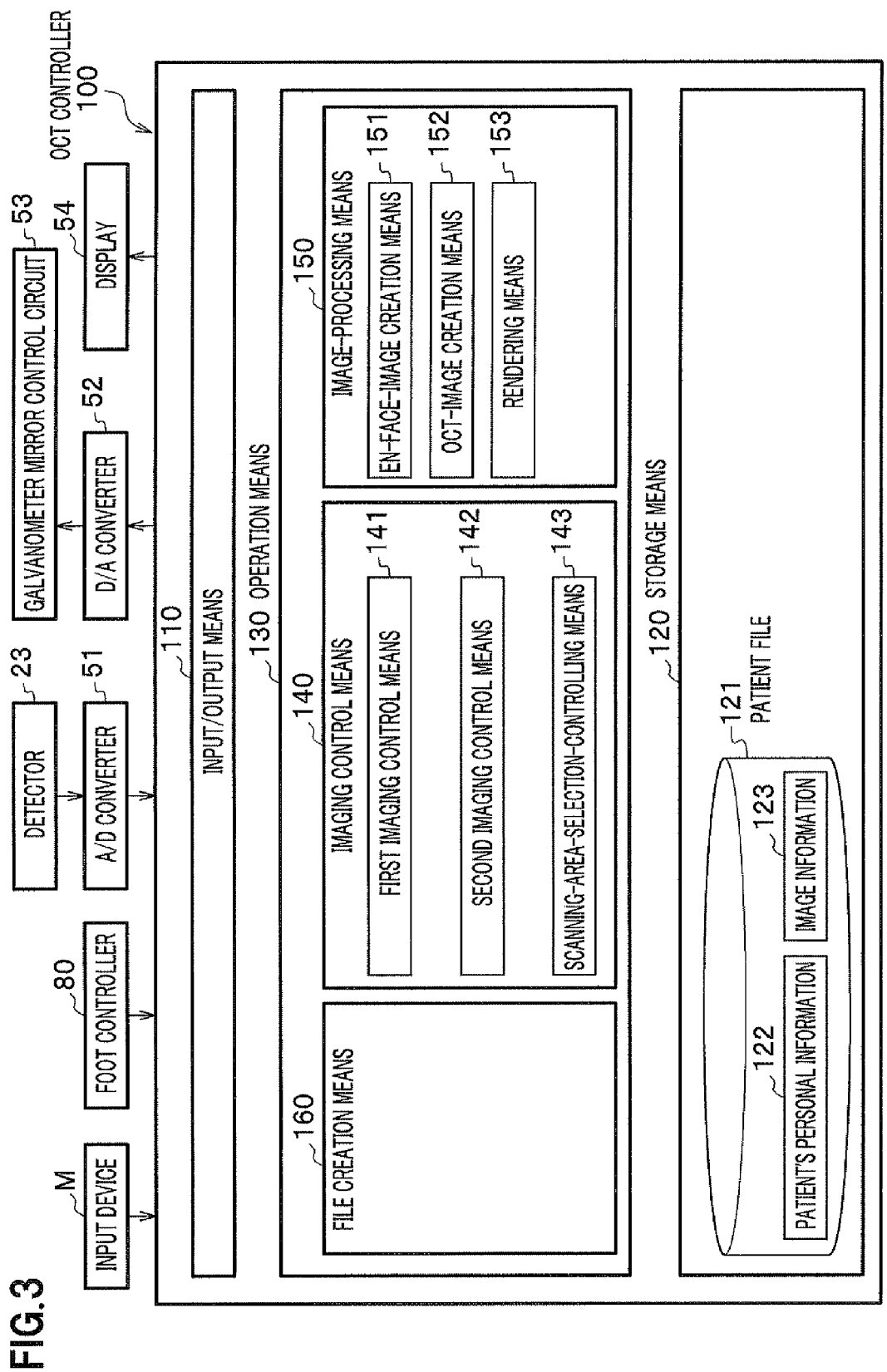
FIG. 3 is a block diagram illustrating functions of an OCT controller according to an embodiment of the present invention.

As illustrated in FIG. 3, the OCT controller 100 includes: a computer constructed with input/output means 110, storage means 120, and operation means 130; and a program installed on this computer.

The input/output means 110 is an interface that transmits and receives various information to and from the outside. The storage means 120 includes, for example, a hard disk and a memory such as a random access memory (RAM) and a read only memory (ROM) so as to store: pre-stored data such as the above program; patients' personal information 122 input from an input device M such as a mouse; operation outputs (e.g., image information 123) of the operation means 130; and other various information.

For example, a central processing unit (CPU) and a graphics processing unit (GPU) are used to run the operation means 130. The operation means 130 includes an imaging control means 140, image-processing means 150, and file creation means 160.

The imaging control means 140 performs imaging with a predetermined imaging mode based on an external input. The imaging control means 140 includes a first imaging control means 141, a second imaging control means 142, and scanning-area-selection-controlling means 143.

The first imaging control means 141 controls and starts imaging when it is determined to receive an input of a measurement command to scan an imaging range of a sample S with laser beam at a predetermined pitch by using a galvanometer mirror 33 so as to determine internal information of the sample S and stops the imaging after an imaging time according to the predetermined pitch. This first imaging control means 141 uses the image-processing means 150 to perform image processing of detection signals obtained by imaging. Based on this measurement command, the image-processing means 150 performs image processing of the detection signals obtained using the galvanometer mirror 33 by scanning the sample with the laser beam at the predetermined pitch. Then, the display 54 displays an optical coherence tomogram of the sample S at the predetermined resolution. This mode operated by the measurement command is one of the predetermined imaging modes.

In an embodiment according to the present invention, when the light source 11 is swept at a sweep rate of 50 kHz, this imaging mode has three measurement modes including "200-measurement", "300-measurement", and "400-measurement".

When the "200-measurement" is selected, A-scan data are obtained at points consisting of 200×200 pixels and their imaging information is displayed.

When the "300-measurement" is selected, A-scan data are obtained at points consisting of 300×300 pixels and their imaging information is displayed.

When the "400-measurement" is selected, A-scan data are obtained at points consisting of 400×400 pixels and their imaging information is displayed.

Here, the image-processing means 150 performs image processing of detection signals obtained by imaging with any of the measurement modes.

The second imaging control means 142 controls and starts imaging when it is determined to receive an input of a preview command to scan the imaging range with the laser beam at a larger pitch than the predetermined pitch by using the galvanometer mirror 33 and stops the imaging when it is determined to receive an input of a command to cancel the preview command. This second imaging control means 142 uses the image-processing means 150 to perform image processing of detection signals obtained by imaging. Based on this preview command, the image-processing means 150 performs image processing of the detection signals obtained using the galvanometer mirror 33 by scanning the sample with the laser beam at the larger pitch than the predetermined pitch. Then, the display 54 displays an optical coherence tomogram of the sample S at a lower resolution than the predetermined resolution. Note that with regard to data on the sample in an optical axis direction (data in an A-direction), the low-resolution image displayed by the preview command has the same resolution as that obtained with the measurement mode. This mode operated by the preview command is one of the predetermined imaging modes.

Hereinafter, this mode is called a preview mode.

In this preview mode according to an embodiment of the present invention, A-scan data are obtained at points, for example, consisting of 128×128 pixels corresponding to the surface of the sample S when the light source 11 is swept at a sweep rate of 50 kHz. Then, their image information is displayed. In addition, the preview mode according to this embodiment is terminated when the above-described measurement command is used to direct any of the measurement modes. That is, the measurement command doubles as a command to cancel the preview command.

While the details are described below, in an embodiment according to the present invention, the preview command or the measurement command can be input into the imaging control means 140 by clicking an operation button "Preview" (see FIG. 9) or "Measure" (see FIG. 9) on a GUI screen by using an input device M such as a mouse.

In addition, according to an embodiment of the present invention, the foot controller 80 can be connected to the control unit section 50 in wired or wireless communication. This foot controller 80 can be used to input the preview command or the measurement command into the imaging control means 140. Specifically, the foot controller 80 includes a first switch and a second switch. When the user uses his/her foot to operate the first or second switch, the foot controller 80 informs the imaging control means 140 of a first switch signal or a second switch signal corresponding to either switch. Accordingly, the second imaging control means 142 determines that an input of the preview command is received when an input of the first switch signal is received from the foot controller 80 and determines that an input of a command to cancel the preview command is received when an input of the second switch signal is received from the foot controller 80. In addition, the first imaging control means 141 determines that an input of the measurement command is received when an input of the second switch signal is received from the foot controller 80. Although detailed imaging requires the user to make the diagnostic probe section 30 contact a patient so as to stabilize image, etc., the foot controller 80 can be controlled in such a manner. This configuration allows the user to press the foot controller 80 by his/her foot even if his/her both hands are occupied. This makes it possible to input the preview command and/or the measurement command even in the above situation.

The foot controller 80 may be, for example, a parallel system in which two pedals that can be switched on/off by foot operation are arranged in parallel and correspond to the first and second switches. The foot controller 80 may be a two-step clutch system in which one pedal (foot switch) operated by a foot doubles as the first and second switches.

In the case of the parallel system, the user presses the foot switch depending on operation of each of the preview command and the measurement command.

In the case of the two-step clutch system, when the user presses the first step of the foot switch, the imaging control means 140 is informed of the first switch signal corresponding to his/her pressing the switch. In addition, when the user presses the foot switch deeper than the first step, the imaging control means 140 is informed of the second signal. In the following description, the foot controller 80 is assumed to be a two-step clutch system.

The scanning-area-selection-controlling means 143 receives an input of an area selected as an imaging range of the sample S from a plurality of predetermined different areas by the user. Then, the scanning-area-selection-controlling means 143 controls and selects a range scanned by the galvanometer mirror 33 according to the input of the area. This scanning-area-selection-controlling means 143 outputs to the galvanometer mirror control circuit 53 a control signal (analog signal) in synchrony with the output cycle of laser beam emitted by the light source 11.

In an example illustrated in FIG. 4A, the range scanned by the galvanometer mirror 33 can be selected from three ranges including the smallest range (S: small), the middle range (M: middle), and the largest range (L: large) in which the surface of the sample S is covered. In this case, the motion rotation angles of the galvanometer mirror 33X in an X-direction and the galvanometer mirror 33Y in a Y-direction are set to a range from −1 degree to +1 degree, a range from −2 degrees to +2 degrees, and a range from −3 degrees to +3 degrees. By doing so, recording areas having three ranges including S, M. and L are assigned. The image obtained by S imaging corresponding to the smallest range can have a higher resolution than the image obtained by L imaging corresponding to the largest range. For example, a measurement mode during the above-described "400-measurement" (at points consisting of 400× 400 pixels) may be selected. At that time, when the scanning area is the smallest range S, the motion rotation angel is within a range from −1 degree to +1 degree to perform the imaging at 400×400 pixels. In a measurement mode during the "400-measurement", the largest range L may be selected as the scanning area. At that time, the motion rotation angle is within a range from −3 degrees to +3 degrees to perform the imaging at 400×400 pixels. That is, the number of pixels per unit area is larger in the smallest range S than in the largest range L, so that a high-resolution image can be produced. Accordingly, an image is taken with the largest range L. Next, an area of interest on the object is targeted. Then, the image is narrowed to the smallest range S. This procedure makes it possible to display the targeted area of interest at a higher resolution.

The image-processing means 150 is to perform image processing of detection signals obtained by imaging.

The image-processing means 150 uses data obtained by imaging of the sample S to generate each of an OCT image with regard to a tomographic plane in a direction along the optical axis toward the sample S, a two-dimensional image with regard to a scanning plane in a direction perpendicular to the optical axis toward the sample S, and a 3D-image of the sample S. The image-processing means 150 is to control and display each generated image on one page of the display 54 as image information regarding the sample S. To achieve this objective, the image-processing means 150 includes en-face-image creation means 151, OCT-image creation means 152, and rendering means 153 as illustrated in FIG. 3.

The en-face-image creation means 151 combines information on the surface of the sample S irradiated with the laser beam and information in a direction (A-direction) along the optical axis toward the sample S to generate an en-face image as a two-dimensional image of the scanning plane (B- and V-directions) perpendicular to the optical axis toward the sample S.

In an embodiment according to the present invention, the en-face-image creation means 151 averages intensities specified by each data (below-described A-scan data) obtained in a direction along the optical axis toward the sample S during imaging of the sample S. These averaged values are each assigned to points in two-dimensional directions scanned by the galvanometer mirror 33 to generate an en-face image. The display 54 displays the en-face image generated. The below describes a flowchart of a process for generating an en-face image. Note that as described below, a 3D-image of the sample S is generated during a course of the en-face image production.

The OCT-image creation means 152 is to generate an OCT image (optical coherence tomogram) with regard to a tomographic plane in a direction along the optical axis toward the sample S from data obtained by imaging the sample S. The display 54 displays the OCT image generated. The below describes a flowchart of a process for generating an OCT image.

The rendering means 153 uses a rendering process to create a 3D-image of the sample S specified from data stored in storage means 120 after the imaging. Then, the display 54 displays the 3D-image.

The file creation means 160 is to create a patient file 121 containing a patient's personal information 122 such as individualized patient information and the tooth number of imaging subject, which information is input by a user using an input device M such as a mouse, before the sample S, a patient's tooth of interest in diagnosis, is imaged. This mode operated by the input operation is called an input mode.

The file creation means 160 processes the patient file 121 according to save operation by the user. The file creation means 160 then links the patient's personal information 122 input before the imaging to the image information 123 after the imaging to store them into the storage means 120. This mode operated by the save operation is called a save data mode. Note that any number of the patient files 121 can be saved.

The file creation means 160 is to search the image information 123 that has been imaged and stored in the patient file 121 according to retrieval operation by the user. Then, the display 54 displays the image information 123. This mode operated by the retrieval operation is called a retrieval mode.

3. How OCT Controller Works

Operation Modes

The following describes an overview of operation modes of an OCT controller 100 according to an embodiment of the present invention.

Preview Mode

Figure 9:
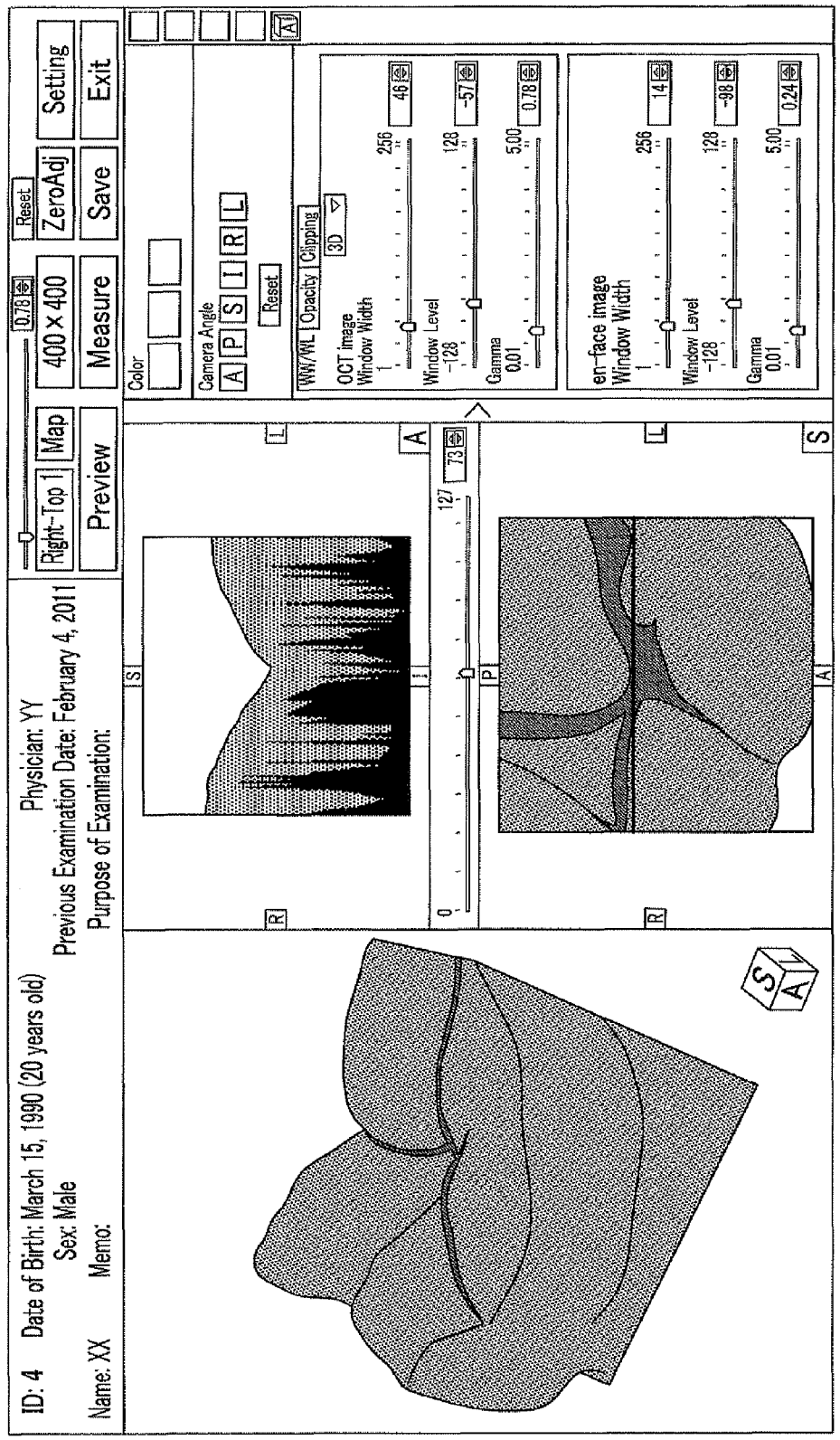
FIG. 9 shows a screen display example regarding image information as obtained using preview imaging by an OCT controller according to an embodiment of the present invention.

The OCT controller 100 starts imaging when it is determined to receive an external input of a preview command and stops the imaging when it is determined to receive an input of a measurement command. In addition, the OCT controller 100 performs image processing of detection signals obtained by imaging during the preview mode. FIG. 9 shows an screen display example of the display 54. Note that FIG. 9 shows an online page while the details are described below. As used herein, the term "online" means that a connection among the diagnostic probe section 30, the optical unit section 10, the control unit section 50, and the display 54 is active and that information obtained with the diagnostic probe section 30 is displayed in real time on the display 54.

Measurement Mode

Figure 10:
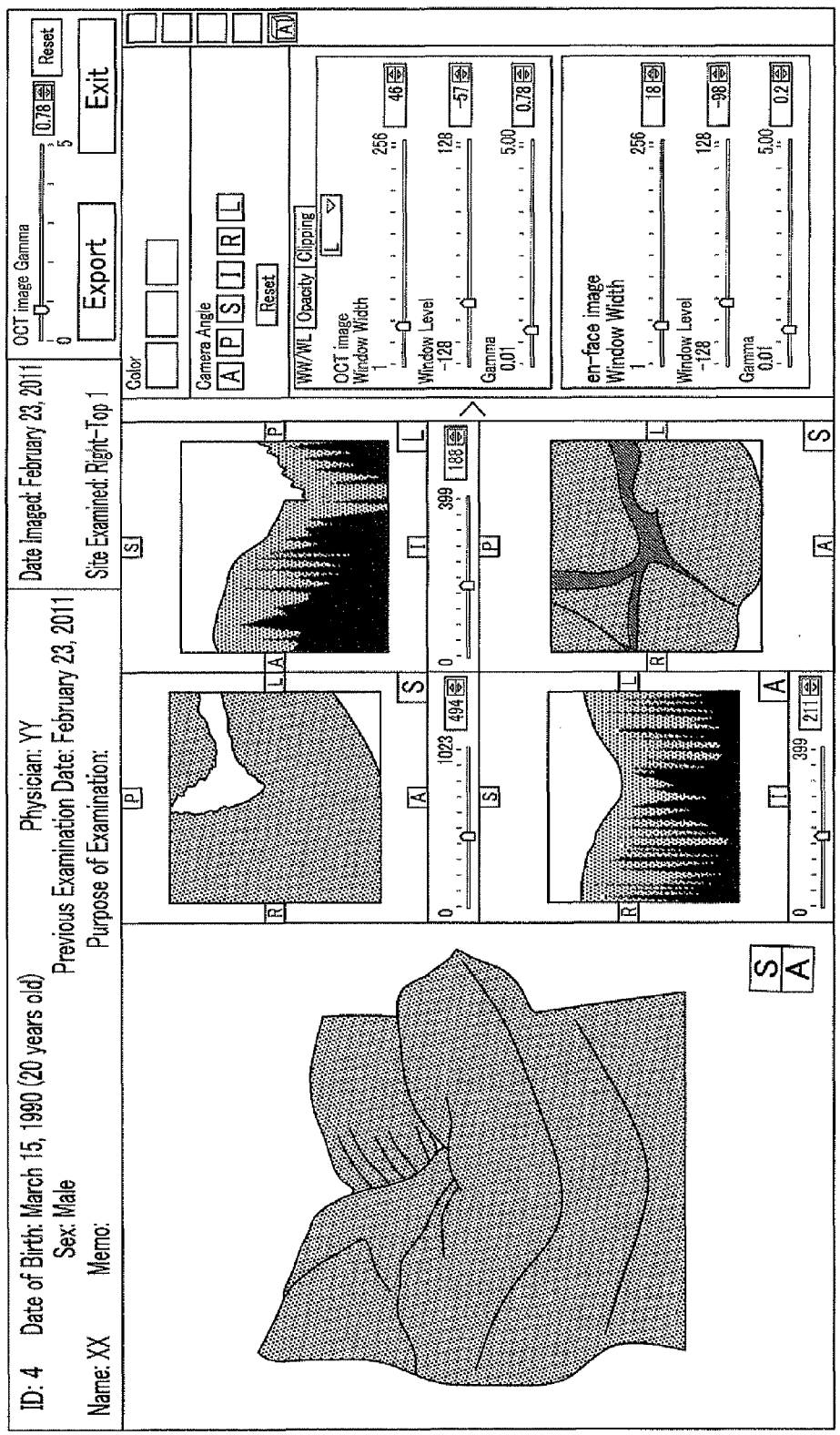
FIG. 10 shows a screen display example regarding image information as obtained using detailed imaging by an OCT controller according to an embodiment of the present invention.

The OCT controller 100 starts imaging when it is determined to receive an external input of a measurement command and stops the imaging after an imaging time according to a predetermined resolution. In addition, the OCT controller 100 performs image processing of detection signals obtained by imaging during the measurement mode. FIGS. 9 and 10 show screen display examples of the display 54. Note that FIG. 9 shows an online page and FIG. 10 shows an offline page while the details are described below. As used herein, the term "offline" means that information obtained with the diagnostic probe section 30 is not displayed on the display 54 as it is but the above information obtained online is stored in the storage means 120, the online process is once exited, and the information is then read to display it on the display 54.

Other Modes

The input mode is an operation mode operated before the preview mode and the measurement mode. In the input mode, the OCT controller 100 is to receive an external input of the patient's personal information 122 such as individualized patient information and the tooth number of imaging subject and to create the patient file 121.

The save data mode is an operation mode operated after the measurement mode. In the save data mode, the OCT controller 100 is to receive an external input of operation to save the image information and to use the patient file 121 to link the patient's personal information 122 to the image information 123 which has already been imaged.

The retrieval mode is an operation mode operated after the save data mode. In the retrieval mode, the OCT controller 100 is to receive an external input of operation to retrieve the image information and is to select the desired image information 123 from the patient files 121 stored in the storage means 120 to display it on the display 54.

Overview of 3D-Scan

With reference to FIGS. 5A, 5B, and 6 (appropriately see FIG. 3), the following describes how the OCT controller 100 generates a two-dimensional OCT image and performs a subsequent 3D-scan.

The positioning of a patient's tooth (sample 5) should be carried out beforehand. In addition, based on a user's operation, the scanning-area-selection-controlling means 143 selects a range scanned by the galvanometer mirror 33 from, for example, the ranges S, M. and L as illustrated in FIG. 4A.

The terms "A-scan", "B-scan", and "V-scan" as illustrated in FIGS. 5A and 5B refer to directions along an A-axis, a B-axis, and a V-axis, respectively, of the diagnostic probe section 30 as illustrated in FIG. 4B. The A-scan illustrated in FIG. 5A corresponds to data representing tomographic information in a depthwise direction from the surface of the sample S. The B-scan corresponds to data representing internal information in a widthwise direction of the sample S. The V-scan illustrated in FIG. 5B corresponds to data representing internal information in a longitudinal direction of the sample S. Each of the A-scan, B-scan, and V-scan data is obtained within the predetermined range. Then, one volume of the 3D-scan can be conducted.

The OCT-image creation means 152 of the image-processing means 150 acquires A-scan data (Step S1). Next, the galvanometer mirror control circuit 53 appropriately changes the X and Y axes under control of the scanning-area-selection-controlling means 143 (Step S2). Note that the below describes an example of timing.

Then, the OCT-image creation means 152 determines whether or not one volume of the A-scan data has been obtained (Step S3). If one volume of the A-scan data has yet to be obtained (Step S3: No), the OCT-image creation means 152 returns the process to Step S1. In contrast, when one volume of the A-scan data has been obtained (Step S3: Yes), the OCT-image creation means 152 performs window processing (Step S4). Subsequently, the OCT-image creation means 152 performs FFT calculation (Step S5).

Specific Examples of 3D-Scan

The following describes specific examples of a 3D-scan.

In an embodiment according to the present invention, A-scan data are obtained at, for example, 1152 points. In this case, a cubic virtual space (a side: L) is simulated according to the position of the sample S positioned to the nozzle tip of the diagnostic probe section 30. The start point of a waveform diagram is set to the point zero which indicates the surface of that virtual space at its nozzle side. Next, the end point of the waveform diagram is set to the 1151st point which indicates another surface of that virtual space at the deepest position side. Then, the A-scan data are obtained at 1152 points. Note that each point not necessarily represents its depth position.

Also, in order to minimize effects due to the finite number of recorded data, a window function is applied to measurement signals within a time domain (i.e., perform window processing). This results in a continuous waveform without a steep transition.

In addition, in order to be able to conduct frequency analysis (FFT processing) on the A-scan data and to make the form of a spectrum after the FFT processing smooth, zero suppression is performed on the A-scan data at 1152 points to produce data at 2048 points. Specifically, 896 points are added to the A-scan data at 1152 points, and the amplitude of the waveform at each point added is treated as 0.

Further, the continuous waveform consisting of 2048 points is subjected to frequency analysis (FFT processing) to calculate 1024 frequency components. Where a reflector and/or a scatterer are present is determined by the results of the frequency analysis: when low frequency components are included in the waveform data, they are localized in a shallow position; and when high frequency components are included in the waveform, they are localized in a deep position.

When the galvanometer mirror 33Y in a Y-direction has a predetermined rotation angle, the axis of the galvanometer mirror 33X in an X-direction is made to slightly rotate. Thus, the irradiation position of the laser beam is shifted along a B-scan in a lateral direction (in an X-axis direction) to obtain A-scan data. This operation is repeated the same number of times as the predetermined number of points (e.g., 128 points) of a B-scan. After that, a slice image (A- and B-scan data) of the cube is acquired.

Here, the slice image of the cube can be generated by converting the amplitudes of A-scan data at 1024 points into brightness values for pixels at 1024 points. The 12-bit brightness value, for example, is represented by an integer of from 0 to 4095. Accordingly, any of from 0 to 4095 may be assigned to each of amplitudes at 1024 points.

Furthermore, the axis of the galvanometer mirror 33Y in a Y-direction is made to slightly rotate. Then, the irradiation position of the laser beam is shifted along a V-scan in a longitudinal direction (in a Y-axis direction) to obtain a slice image (A- and B-scan data). This operation is repeated the same number of times as the predetermined number of points (e.g., 128 points) of a V-scan. Finally, data of the cube is completed.

For example, during the preview, 128 points can be selected as the number of the predetermined points in a B-scan and a V-scan. During the measurement, this number can be selected from, for example, 200 points, 300 points, and 400 points.

Process for Creating En-Face Image

With reference to FIG. 7, the following describes a process for creating an en-face image.

Each process at Steps S11 to S15 is substantially the same as each process at Steps S1 to S5. Accordingly, the description is omitted. Subsequently, the en-face-image creation means 151 of the image-processing means 150 adds A-scan data (Step S16). Here, when 1024 frequency components, for example, are calculated as the results of the FFT processing of the A-scan data, all the 1024 frequency components are added to calculate a total.

Next, the en-face-image creation means 151 averages the total of the A-scan data (Step S17). Here, when 1024 frequency components, for example, are calculated, the total of the A-scan data is divided by 1024 to make an average. The process for averaging frequency components at these Steps S16 and 17 corresponds to a process for determining a pixel value of an image (B-×V-scan data) in a two-dimensional plane having a widthwise direction (B-scan) and a longitudinal direction (V-scan) of the sample S (see, FIGS. 5A and 5B).

Then, the en-face-image creation means 151 determines whether or not the process for averaging frequency components has been completed on the B-×V-scan data (Step S18). If the process has yet to be completed on the B-×V-scan data (Step S18: No), the en-face-image creation means 151 returns the process to Step S16. In contrast, if the process has been completed on the B-×V-scan data (Step S18: Yes), the en-face-image creation means 151 terminates the process. For example, during the preview, an en-face image is created at a resolution with 128×128 pixels. In addition, for example, during the 400×400 measurement, an en-face image is created at a resolution with 400×400 pixels.

Specific Example of Timing During Image Processing

With reference to FIGS. 8A, 8B, 8C, 8D, and 8E, the following describes a specific example of timing during image processing. FIGS. 8A, 8B, 8C, 8D, and 8E show an example of a timing chart for image-processing by an OCT controller 100 according to an embodiment of the present invention.

FIG. 8A shows a sweep trigger (see FIG. 2) output from the light source 11.

FIG. 8B shows a start trigger (analog output) output from the D/A converter circuit 52. The start tiger is a pulse waveform similar to that of FIG. 8A.

FIG. 8C shows an analog output voltage regarding an X-direction, which voltage is output from the galvanometer mirror control circuit 53 to the galvanometer mirror 33X in an X-direction.

FIG. 8D shows an analog output voltage regarding a Y-direction, which voltage is output from the galvanometer mirror control circuit 53 to the galvanometer mirror 33Y in a Y-direction.

FIG. 8E shows a clock (i.e., ck; see FIG. 2) that is output by the light source 11 and that is used to generate an OCT image.

In this example, the light source 11 has a sweep rate at 50 kHz. The slight motion (rotation) and stop of the galvanometer mirror 33X are in synchrony with this sweep rate and are repeated at 50 kHz (a pulse cycle of 20 us). Note that the "us" denotes a microsecond.

At the time S in FIG. 8A, the preview or the measurement starts.

When a period of 15 pulses after the start has passed, a 3D-scan is initiated at the time A in FIG. 8A. At the time B in FIG. 8A, one volume of the 3D-scan is completed. As for the measurement, the measurement is completed at the time B. During the preview, the process returns to the time A following the time B, and the process then repeats.

As illustrated in FIG. 8C, the analog output voltage regarding an X-direction is −Vx at the time A. Then, the analog output voltage becomes +Vx at the 158th pulse after the time A (i.e., an outbound route for mirror). At the 30th pulse after that, the analogue output voltage becomes −Vx again (i.e., an inbound route for mirror). Following that, the process repeats until one volume of the 3D-scan is completed.

The 158 pulses illustrated in FIG. 8C correspond to 128 points in a B-scan. The 128 points are required but additional 30 points are obtained to produce data at 158 points. The reason for this is as follows. Specifically, because both ends where the galvanometer mirror 33 has the maximum tilt angle have a little position change, data at 15 points from both the ends cannot be under practical use.

Note that when a B-scan is measured at 200 points, +Vx is reached at the 230th pulse. In the case of a measurement at 300 points, +Vx is reached at the 330th pulse. In the case of a measurement at 400 points, +Vx is reached at the 430th pulse.

In addition, the inbound route for mirror has a shorter movement time than the outbound route for mirror. This is because data acquired during the inbound route for mirror are not used. At this occasion, the operating speed of the galvanometer mirror 33 is limited (e.g., the maximum is at 100 Hz when the mirror swings between ±30 degrees). Consequently, it is necessary to return the galvanometer mirror 33 in such a speed that it does not get damaged.

As illustrated in FIG. 8D, the analog output voltage regarding a Y-direction stays at −Vy from the time A to the time at the 158th pulse. A slight shift occurs at the 159th pulse (after a B-scan is performed). Following that, a slight shift repeats similarly after another B-scan is performed. The analog output voltage becomes +Vy at a predetermined time before one volume of the 3D-scan has been completed (at the 30th pulse before the time B) (i.e., an outbound route for mirror). The analog output voltage becomes −Vy again at the 30th pulse after that (i.e., an inbound route for mirror).

As illustrated in FIG. 8E, in order to create an image, data is sampled at 50 kHz (i.e., a pulse cycle of 20 us) from the time A to the time B. Then, the first frame of the slice image is created (i.e., the first frame is imaged) using, for example, a period of 128 pulses during the outbound route for mirror (a period of 158 pulses) from the time A. Note that as described above, data acquired during the 15 pulses at the beginning and the end are not used. Likewise, whenever a B-scan is performed, each frame of the slice image is generated. In this example, 128 frames of the slice image are created as V-scan data.

4. Screen Display Examples of Display

Online Page

With reference to FIG. 9, the following describes a specific example of an online page.

This online page displays a 3D screen placed in the left side in FIG. 9, an en-face screen placed in the bottom center side in FIG. 9, and an OCT screen placed in the top center side in FIG. 9.

In the example illustrated in FIG. 9, a cubic virtual space is simulated according to the position of the sample S (a molar) positioned to the nozzle tip of the diagnostic probe section 30. For example, in the en-face screen, each side of the cube is represented by S side (the sample S surface in the en-face image: the upper surface), A side (the anterior side viewed from the sample S surface in the en-face image), P side (the posterior side viewed from the sample S surface in the en-face image), R side (the right side viewed from the sample S surface facing the anterior side), L side (the left side viewed from the sample S surface facing the anterior side), and I side (the opposite surface of the sample S surface in the en-face image: the inferior surface).

With regard to the 3D screen, the "Camera Angle" shown in the right side of the online page is used to select A, P, S, I, R. or L side. By doing so, a 3D-image viewed from the desired side is displayed in real time. Note that the illustrated example shows an anterior-left image of the sample S viewed from the S side (the sample S surface in the en-face image).

The en-face screen displays an en-face image which combines information on the surface of the sample S viewed from the S side (the sample S surface in the en-face image) and information in a depthwise direction toward the sample S. Internal information, which cannot be observed in itself from the outer surface, appears on the en-face image.

The OCT screen displays an OCT image in a cut-out plane (tomographic plane) that is cut out in a plane parallel to the A side (the anterior side viewed from the sample S surface in the en-face image) and is cut at the horizontal line drawn across the approximate center in the en-face image. In the example illustrated in FIG. 9, a tomographic image viewed from the A side to the P side is displayed as an OCT image. Note that a tomographic image viewed from the P side to the A side may be instead displayed as an OCT image.

The top-left side in the online page displays various information such as a patient's personal information.

The top-right side in the online page shows the arrangement of icons "Preview", "Measure", "400×400", "ZeroAdj", "Save", "Setting", "Exit", etc.

The "Preview" indicates a button for inputting a preview command. If this button is pressed, each image is displayed in real time on the 3D screen, the en-face screen, and the OCT screen. For example, a 3D image is updated about every one second. If the user moves the nozzle tip of the diagnostic probe section 30, the movement-associated image information (the preview image) can be acquired. Note that the save is not anticipated for the preview image.

The "Measure" indicates a button for inputting a measurement command. If the "Measure" button is pressed during the preview, detailed imaging starts while the preview command is canceled. Then, the imaging is automatically completed after an imaging time according to the resolution which has been selected at that time. The detailed imaging is imaging followed by the save, and is performed while the sample S is fixed. As used herein, the term "fixed" refers to contacting the diagnostic probe section 30 to the nozzle tip. At that instance, a patient is requested not to be moved. In the case of the "400×400" resolution, the detailed imaging is completed in about three seconds. When the resolution is lower than that, the imaging should be completed in less than three seconds.

The "400×400" indicates a button for inputting a resolution. This button is set to "128×128" during the preview. When the button is pressed before the measurement, the user can select the resolution from any of the "200×200", "300×300", and "400×400".

The "ZeroAdj" indicates a button, used at calibration before data recording, for performing initialization zero-point adjustment by closing a shutter 31 (see FIG. 2) of the diagnostic probe section 30 when optical system noise, etc., is used as background data for measurement. The OCT-image creation means 152 reduces effects of the noise by subtracting the background data from recording data when data is scanned. Note that if the "ZeroAdj" is performed during the preview, it is unnecessary to perform it during the measurement.

The "Save" indicates a button for saving the scanned data as binary data. Here, the saved data can be read and displayed on the offline page described below. Note that the patient file 121 (see FIG. 3) is created before the preview and the patient's personal information 122 should be input. The patient's personal information contains his/her name as well as the tooth number of imaging subject, etc. This input is prerequisite, followed by pressing the "Save" button. This operation can link the suitable image information 123 to the patient file 121 (see FIG. 3).

The foot controller 80 may be used to input a measurement command into the imaging control means 140. In this case, after completion of the detailed imaging, the screen of the display 54 changes to the screen which should be displayed by pressing the "Save" button. Then, the screen on the save operation page displays a message whether or not the image information obtained is saved, and the "Yes" or "No" button. When the user steps on and presses the first step of the pedal of the foot controller 80, the user can select either "Yes" or "No". Here, when the "Yes", for example, is selected, the user may further press another step, namely, the second step of the foot controller 80. At this time, a command to save the image information becomes final.

Note that when the user steps on and presses the first step of the pedal to select the "Yes", the user may step off his/her foot. At that time, the pedal returns to the original position and the currently-selected "Yes" does not become final. Then, when the user steps on and presses the first step of the pedal of the foot controller 80 again, the display changes to the "No". Following that, the tentative "Yes" or "No" can be likewise switched.

Alternatively, when the parallel system is used as an alternative for the two-step clutch system, the user presses down each foot switch corresponding to each of the "Yes" and the "No". As used herein, each foot switch corresponding to each of the "Yes" and the "No" can double as a function to output the first and the second switch signals by using the switches. The foot controller 80, however, may have another specialized foot switch.

The "Setting" indicates a button for inputting a range scanned by the galvanometer mirror 33. When this button is pressed, the user can select the area from any of three ranges: S, M, and L by using the pull-down menu. At this time, based on the input operation data, the scanning-area-selection-controlling means 143 (see FIG. 3) determines a range scanned by the galvanometer mirror 33.

The "Exit" indicates a button for exiting this online page to return to the previous page or the top page.

The right side of the online page displays slider bars for adjusting images displayed on the 3D screen, all the image displays, and the A screen.

The "Window Width" is a bar for determining an adjustment width regarding contrast.

The "Window Level" is a bar for determining a median of the "Window Width".

The "Gamma" is a bar for emphasizing a week signal so as to be able to adjust the contrast. Note that, the illustrated example shows how the adjustment looks like by using the slider below to designate the "3D screen".

Offline Page

With reference to FIG. 10, the following describes a specific example of an offline page.

The left side of the offline page in FIG. 10 displays, as image information, a 3D-image of which the saved data is used to perform rendering.

The OCT image arranged at the center left-top side in FIG. 10 shows a tomogram cut in a cross section parallel to the S side (the sample S surface in the en-face image).

The OCT image arranged at the center right-top side in FIG. 10 shows a tomogram cut in a cross section parallel to the L side.

The OCT image arranged at the center left-bottom side in FIG. 10 shows a tomogram cut in a cross section parallel to the A side.

The en-face image arranged at the center right-bottom side in FIG. 10 shows an en-face image viewed from the S side (the sample S surface in the en-face image).

The top-left side in the offline page displays various information such as a patient's personal information.

The top-center side in the offline page displays a Date Imaged and a Site Examined.

The top-right side in the offline page shows the arrangement of operation buttons "Export", "Exit", etc.

The "Export" indicates a button for converting the imaging data for output.

The "Exit" indicates a button for exiting this offline page to return to the previous page or the top page.

According to an embodiment of the present invention, the OCT controller 100 displays an OCT image at a low resolution during the preview mode and an OCT image at a high resolution during the measurement mode. Accordingly, the user, for example, can beforehand obtain an OCT image used for measurement and/or diagnosis while the preview mode is used to keep the image at a lower resolution. In addition, the preview mode can display an OCT image which is imaged and image-processed as a real-time moving image. As a result, the preview mode can repeat and easily display different low-resolution OCT images. Accordingly, the user can quickly find out a desired tomographic plane as a tomogram of the sample S. This information can be used to allow for fast acquisition of a desired tomogram of the sample S at a high resolution.

Hereinabove, the embodiments of the present invention have been described. The present invention, however, is not limited to the above embodiments, and can be put into practice within an extent not departing from its scope. For example, in the preview mode, the OCT controller 100 starts imaging when it is determined to receive an external input of a preview command and stops the imaging when it is determined to receive an input of a measurement command. Of course, a command to cancel the preview command can be separated from the input of the measurement command.

In addition, the present invention is not limited to the high coherent light source 11 with a coherence length of 10 mm or more as performance of its laser beam.

Also, in an embodiment of the present invention, the SS-OCT system is used for description. The SD-OCT or TD-OCT system, however, may be employed.

Further, with regard to the diagnostic probe section 30, it is preferable to use the nozzle tip illustrated in FIG. 4B when the sample S is a front tooth. When the sample S is a molar, it is preferable that the nozzle tip is fitted with a member capable of reflecting laser beam at a right angle.

In the present invention, the object is not limited to a tooth. Moreover, the present invention may apply to non-destructive inspection and medical instruments other than those used in dentistry.

EXPLANATION OF REFERENCE NUMERALS 1, 1A OCT apparatus (Optical coherence tomography apparatus)
10 Optical unit section (Optical unit)
11 Light source
12 Coupler
13 Sample arm
14 Circulator
15 Polarization controller
16 Coupler
17 Reference arm
18 Circulator
19 Collimator lens
20 Condensing lens
21 Reference mirror
22 Polarization controller
23 Detector
30 Diagnostic probe section (Probe)
31 Shutter
32 Collimator lens
33 Galvanometer mirror (Scanning mechanism)
33X Galvanometer mirror in an X-direction
33Y Galvanometer mirror in a Y-direction
34 Condensing lens
50 Control unit section (Control unit)
51 A/D converter circuit
52 D/A converter circuit
53 Galvanometer mirror control circuit
54 Display
60 Cable
70 Single-joint arm
70A Multiple-joint arm
80 Foot controller
100 OCT controller
110 Input/output means
120 Storage means
121 Patient file
122 Patient's personal information
123 Image information
130 Operation means
140 Imaging control means
141 First imaging control means
142 Second imaging control means
143 Scanning-area-selection-controlling means
150 Image-processing means
151 En-face-image creation means
152 OCT-image creation means
153 Rendering means
160 File creation means
M Input device
S Sample (Object)

The invention claimed is:

1. A controller for an optical coherence tomography apparatus, comprising:
an imaging control means for imaging with a predetermined imaging mode based on an external input; and image-processing means for performing image processing of an detection signal as obtained at the imaging,
the imaging control means comprising: a first imaging control means for starting imaging when it is determined to receive an input of a measurement command to scan an imaging range of an object with laser beam at a predetermined pitch by using a scanning mechanism so as to determine internal information of the object and for stopping the imaging after an imaging time according to the predetermined pitch; and a second imaging control means for starting imaging when it is determined to receive an input of a preview command to scan the imaging range with the laser beam at a larger pitch than the predetermined pitch by using the scanning mechanism and for stopping the imaging when it is determined to receive an input of a command to cancel the preview command,
wherein the optical coherence tomography apparatus comprises:
an optical unit comprising: a light source for periodically emitting the laser beam on the object; and a detector for detecting the internal information of the object;
a probe comprising the scanning mechanism which can perform two-dimensional scanning with the laser beam, the probe guiding the laser beam emitted through the optical unit to the object and guiding light reflected by the object to the optical unit; and
a control unit comprising: the controller for controlling generation of an optical coherence tomogram of the object from data converted from the detection signal of the detector while performing imaging by controlling the scanning mechanism in synchrony with the laser beam; and a display for displaying the optical coherence tomogram.

2. The controller for an optical coherence tomography apparatus according to claim 1, wherein the control unit comprises a foot controller connected to the imaging control means in wired or wireless communication, the foot controller comprising a first switch and a second switch,
wherein when a user uses his/her foot to operate either the first switch or the second switch, the imaging control means is informed of a first or second switch signal corresponding to the first or second switch;
when the second imaging control means receives an input of the first switch signal from the foot controller, it is determined to receive an input of the preview command;
when the second imaging control means receives an input of the second switch signal from the foot controller, it is determined to receive an input of a command to cancel the preview command; and
when the first imaging control means receives an input of the second switch signal from the foot controller, it is determined to receive an input of the measurement command.

3. The controller for an optical coherence tomography apparatus according to claim 2, further comprising scanning-area-selection-controlling means for controlling selection of a range scanned by the scanning mechanism according to an area of interest,
wherein the area is selected by the user from a plurality of predetermined different areas as imaging ranges for the object; and the area is input to the imaging control means.

4. The controller for an optical coherence tomography apparatus according to claim 2, wherein the image-processing means uses data obtained by taking an image of the object to generate: an optical coherence tomogram with respect to a tomographic plane in a direction along an optical axis toward the object; a two-dimensional image with respect to a scanning plane perpendicular to the optical axis toward the object; and a three-dimensional image of the object, and
wherein the image-processing means controls and displays each generated image on one page of the display as image information regarding the object.

5. The controller for an optical coherence tomography apparatus according to claim 4, wherein the image-processing means generates, as the two-dimensional image with regard to the scanning plane perpendicular to the optical axis toward the object, an en-face image which combines information on the surface of the object irradiated with the laser beam and information on the object in a direction along the optical axis.

6. The controller for an optical coherence tomography apparatus according to claim 1, further comprising scanning-area-selection-controlling means for controlling selection of a range scanned by the scanning mechanism according to an area of interest,
wherein the area is selected by the user from a plurality of predetermined different areas as imaging ranges for the object; and the area is input to the imaging control means.

7. The controller for an optical coherence tomography apparatus according to claim 1, wherein the image-processing means uses data obtained by taking an image of the object to generate: an optical coherence tomogram with respect to a tomographic plane in a direction along an optical axis toward the object; a two-dimensional image with respect to a scanning plane perpendicular to the optical axis toward the object; and a three-dimensional image of the object, and
wherein the image-processing means controls and displays each generated image on one page of the display as image information regarding the object.

8. The controller for an optical coherence tomography apparatus according to claim 7, wherein the image-processing means generates, as the two-dimensional image with regard to the scanning plane perpendicular to the optical axis toward the object, an en-face image which combines information on the surface of the object irradiated with the laser beam and information on the object in a direction along the optical axis.

9. A method for controlling an optical coherence tomography apparatus, the optical coherence tomography apparatus comprises:
an optical unit comprising: a light source for periodically emitting laser beam on an object; and a detector for detecting internal information of the object;
a probe comprising: a scanning mechanism which can perform two-dimensional scanning with the laser beam, the probe guiding the laser beam emitted through the optical unit to the object and guiding light reflected by the object to the optical unit; and
a control unit comprising: the controller for controlling generation of an optical coherence tomogram of the object from data converted from a detection signal of the detector while performing imaging by controlling the scanning mechanism in synchrony with the laser beam; and a display for displaying the optical coherence tomogram, comprising the steps of:
stating imaging when it is determined to receive an input of a measurement command to scan an imaging range of the object with the laser beam at a predetermined pitch by using the scanning mechanism so as to determine the internal information of the object and stopping the imaging after an imaging time according to the predetermined pitch, as one of predetermined imaging modes based on an external input for a controller;
starting imaging when it is determined to receive an input of a preview command to scan the imaging range with the laser beam at a larger pitch than the predetermined pitch by using the scanning mechanism and stopping the imaging when it is determined to receive an input of a command to cancel the preview command, as another of the predetermined imaging modes based on an external input for the controller; and
image-processing a detection signal as obtained by the imaging of either imaging mode.

10. A non-transitory computer-readable recording medium in which a program for controlling a controller for an optical coherence tomography apparatus is stored, the controller comprising:
an imaging control means for imaging with a predetermined imaging mode based on an external input; and image-processing means for performing image processing of an detection signal as obtained at the imaging,
the imaging control means comprising: a first imaging control means for starting imaging when it is determined to receive an input of a measurement command to scan an imaging range of an object with laser beam at a predetermined pitch by using a scanning mechanism so as to determine internal information of the object and for stopping the imaging after an imaging time according to the predetermined pitch; and a second imaging control means for starting imaging when it is determined to receive an input of a preview command to scan the imaging range with the laser beam at a larger pitch than the predetermined pitch by using the scanning mechanism and for stopping the imaging when it is determined to receive an input of a command to cancel the preview command, wherein the optical coherence tomography apparatus comprises:

an optical unit comprising: a light source for periodically emitting the laser beam on the object; and a detector for detecting the internal information of the object;

a probe comprising the scanning mechanism which can perform two-dimensional scanning with the laser beam, the probe guiding the laser beam emitted through the optical unit to the object and guiding light reflected by the object to the optical unit; and a control unit comprising: the controller for controlling generation of an optical coherence tomogram of the object from data converted from the detection signal of the detector while performing imaging by controlling the scanning mechanism in synchrony with the laser beam; and a display for displaying the optical coherence tomogram.

11. A non-transitory computer-readable recording medium in which a program for executing a method for controlling an optical coherence tomography apparatus is stored, the method comprising the steps of:

stating imaging when it is determined to receive an input of a measurement command to scan an imaging range of an object with laser beam at a predetermined pitch by using a scanning mechanism so as to determine internal information of the object and stopping the imaging after an imaging time according to the predetermined pitch, as one of predetermined imaging modes based on an external input for a controller;

starting imaging when it is determined to receive an input of a preview command to scan the imaging range with the laser beam at a larger pitch than the predetermined pitch by using the scanning mechanism and stopping the imaging when it is determined to receive an input of a command to cancel the preview command, as another of the predetermined imaging modes based on an external input for the controller; and image-processing a detection signal as obtained by the imaging of either imaging mode, wherein the optical coherence tomography apparatus comprises:

an optical unit comprising: a light source for periodically emitting the laser beam on the object; and a detector for detecting the internal information of the object;

a probe comprising the scanning mechanism which can perform two-dimensional scanning with the laser beam, the probe guiding the laser beam emitted through the optical unit to the object and guiding light reflected by the object to the optical unit; and a control unit comprising: the controller for controlling generation of an optical coherence tomogram of the object from data converted from the detection signal of the detector while performing imaging by controlling the scanning mechanism in synchrony with the laser beam; and a display for displaying the optical coherence tomogram.

* * * * *